United States Patent
Schäfer et al.

[11] Patent Number: 6,153,101
[45] Date of Patent: *wx.-99,-9999

[54] DEVICE FOR ION-EXCHANGE CHROMATOGRAPHY AND METHOD OF CYCLICALLY REGENERATING A PLURALITY OF SUPPRESSORS OF SUCH A DEVICE

[75] Inventors: Helwig Schäfer; Markus Läubli; Paul Zähner, all of Herisau, Switzerland

[73] Assignee: Metrohm AG, Herisau, Switzerland

[*] Notice: This patent issued on a continued prosecution application filed under 37 CFR 1.53(d), and is subject to the twenty year patent term provisions of 35 U.S.C. 154(a)(2).

[21] Appl. No.: 08/584,067

[22] Filed: Jan. 11, 1996

[30] Foreign Application Priority Data

Feb. 1, 1995 [CH] Switzerland ............... 272/95

[51] Int. Cl.$^7$ ................................................. B01D 15/08
[52] U.S. Cl. ......................... 210/635; 210/656; 210/659; 210/198.2; 436/150; 436/161
[58] Field of Search ................... 210/635, 656, 210/659, 676, 198.2; 436/161, 150

[56] References Cited

U.S. PATENT DOCUMENTS

| | | | |
|---|---|---|---|
| 3,920,397 | 11/1975 | Small et al. | 210/656 |
| 4,017,262 | 4/1977 | Small et al. | 210/284 |
| 4,242,097 | 12/1980 | Rich | 210/656 |
| 4,265,634 | 5/1981 | Pohl | 210/656 |
| 4,314,823 | 2/1982 | Rich | 210/656 |
| 4,455,233 | 6/1984 | Pohl | 210/656 |
| 4,474,664 | 10/1984 | Stevens | 210/656 |
| 4,500,432 | 2/1985 | Poole | 210/659 |
| 4,695,386 | 9/1987 | Berry | 210/676 |
| 4,766,082 | 8/1988 | D'Autry | 210/656 |
| 4,808,317 | 2/1989 | Berry | 210/676 |
| 4,966,695 | 10/1990 | Joshua | 210/659 |
| 4,969,993 | 11/1990 | Nash | 210/656 |
| 5,061,628 | 10/1991 | Roberts | 435/199 |
| 5,107,908 | 4/1992 | Newhouse | 210/656 |
| 5,395,521 | 3/1995 | Jagadeeswaran | 210/656 |
| 5,443,734 | 8/1995 | Fetner | 210/656 |
| 5,478,475 | 12/1995 | Morita | 210/676 |
| 5,567,307 | 10/1996 | Karmarkar | 210/656 |
| 5,597,734 | 1/1997 | Small et al. | 210/656 |

FOREIGN PATENT DOCUMENTS 63-91558 10/1986 Japan .................... 210/656

OTHER PUBLICATIONS

ISA Transactions vol. 18 No. 2, "On–Stream Ion Chromatography; an Aid to Energy Conservation"—T. Miller 1979 pp. 59–63.

Analytica Chimica Acta 130 (1981), pp. 1–8 Fast Determination of Anions by Computerized Ion Chromatography Couples with Selective Detectors.

Analytica Chimica Acta 156 (1984), pp. 169–180 "Linear Calibration in Ion Chromatography by Calculating Total Amounts of Sample from Measured Conductivity Data".

"Ion Chromatography of Inorganic Trace Constituents in Water" (Marcelis Jan van Os) geboren op Oct. 5, 1953 pp. 95, 102, 128, & 143.

"Moderne Chromatographie Von Ionen" Seminar Und Workshop 1982, Doz. Dr. Hans Wegscheider pp. 1–9.

"Ion Chromatography in Water" (Ionen–Chromatographie in Niederschlagswasser) K.P. Muller (1984) pp. 345–346.

Abstract—"Improvement of Anion Detection by Suppressor Column Modification"—Petten (Netherlands) 1980 (1 Page).

*Primary Examiner*—Ernest G. Therkorn
*Attorney, Agent, or Firm*—Shoemaker and Mattare

[57] ABSTRACT

In order to regenerate a plurality of suppressors (6, 6a, 6b) that are inserted alternatingly into a device for ion-exchange chromatography, apart from an analysis branch (9), at least one additional treatment branch (10, 10a) is anticipated, through which a treatment agent (7, 7a) can be fed. The analysis branch (9) and the treatment branch (10, 10a) each possess a gap (34) in which the suppressors (6, 6a, 6b) can be alternatingly inserted. In order to insert a suppressor in a pipework branch, the suppressor is moved relative to the pipework branch until the connection openings (36a, 36b) of the suppressor are aligned with the corresponding pipe openings (35) of the gap of the pipework branch concerned.

2 Claims, 5 Drawing Sheets

DEVICE FOR ION-EXCHANGE CHROMATOGRAPHY AND METHOD OF CYCLICALLY REGENERATING A PLURALITY OF SUPPRESSORS OF SUCH A DEVICE

The invention concerns a device for ion-exchange chromatography and a method of cyclically regenerating a plurality of suppressors employed in a device for ion-exchange chromatography.

Ion-exchange chromatography is a form of liquid chromatography used for the analysis of ionic species. Electrolytes are used for the elution, retention times of the individual ions being determined by means of their affinity to stationary phases. The detection of separated ions is as a rule achieved by measuring conductivity. Using the so-called single-column technique, the eluate running from the separating column is fed directly to a detector. However, this is accompanied by the disadvantage that the detection of the ions to be analysed is impaired by the conductivity of the elution agent employed. Conductivity of the elution agent will only be subjected to inconsequential change by the ions of the analysis sample, while the detection of this change is associated with considerable difficulties.

As a solution to the problem, some time ago the use of the so-called twin-column technique was recommended, wherein the eluate running from the separation column is first of all fed to a subsequent suppressor column, and is only then fed to the detection unit. The suppressor column contains an ion exchanger that is suitable for reducing the high background conductivity of the elution agent. At the same time, the analysis sample is, when possible, transformed into a more conductive form. In order to reduce the background conductivity, ion exchange will take place in the suppressor column. Since the suppressor column only possesses a limited capacity with regard to ion exchange, from time to time it requires regeneration. To that end, at least one treatment liquid is fed through the suppressor. As a rule, for a first treatment liquid, it is an acid or an alkaline solution that is used to load the ion exchanger. For a second treatment liquid, it can, for example, be water that is fed through the suppressor column. For this purpose, various piping is required, connected to the suppressor column.

In order to facilitate this procedure, the use of two adjacent suppressor columns has already been recommended in U.S. Pat. No. 3,920,397, the said columns being connected via selector valves with the appropriate connection piping so that, through valve settings, alternatingly one of the supressor columns can be consecutively connected to the various treatment agent sources, while the other is connected with the separation column outlet and used in an analytical process. By switching over the valve, the valve settings enable the substitution of the suppressor coupled into the analysis circuit between the separation column and the detector with a regenerated suppressor when required, as well as connection of the substituted suppressor with a treatment medium source for the purposes of regeneration. The valve arrangement required for this purpose is, of course, very complex: each suppressor has two connection openings, and each of these connection openings requires connection to a valve through which it can be connected with different pipes, that likewise require connection to the valve.

It is therefore a purpose of the invention to create an opportunity for cyclic regeneration of a plurality of suppressors that permits a simple construction for the device required for connection of the different pipes to the individual suppressors. According to the invention, this purpose is fulfilled by a method possessing the features of claim 1 and a device possessing the features of claim 3.

Contrary to state-of-the-art systems, with which the different pipes are allocated to a suppressor by means of selection of a valve setting, here, in order to produce the desired allocation, the suppressors themselves are moved in relation to the pipework. To this end, a plurality of pipework branches are used into which the suppressors are inserted alternatingly. A first pipework branch connects the outlet of the separation column with a detector. In the following, this pipework branch will be referred to as an analysis branch. Additionally, at least one further pipework branch is employed, and in the following this will be referred to as a treatment branch. Each pipework branch possesses a gap, into which a suppressor can be inserted. To this end, the suppressor can be moved in relation to the pipework branch into a position in which the said suppressor bridges the gap, as a section of pipe, in the flow line branch concerned.

During an analysis period, respectively one of the suppressors is inserted, as a section of pipe, into the analysis branch. After in each case one analysis period, this suppressor will be substituted by a regenerated suppressor and, for the purposes of regeneration, the substituted suppressor will be consecutively inserted into one or more treatment branches, through which in each case at least one treatment agent will be fed through the inserted suppressor. The duration of an analysis period can be determined in different ways. A fixed time interval can be involved, for example, after which the suppressor inserted in the analysis branch will be substituted by a regenerated suppressor. Preferably, the duration of an analysis period is determined by the duration of the analyses to be carried out, however, wherein the suppressor is substituted after analysis of one or more samples. It is particularly advantageous if the suppressor inserted into the analysis branch is substituted by a regenerated suppressor after the analysis of in each case one sample. This has the advantage that the analysis of each individual sample will be commenced with a freshly regenerated suppressor, so that the same basic conditions will apply to all analyses.

If the suppressor due for regeneration is to be inserted into a plurality of treatment branches, this will as a rule occur in a fixed, prescribed sequence, so that the different treatment liquids will be fed through the suppressor in a definite sequence. The suppressor so regenerated will later be inserted into the analysis branch as a substitute for another used suppressor. In this way, the suppressors will be alternatingly inserted into the analysis branch, and cyclically regenerated.

Through the use of individual pipework branches, and the fact that, when inserting a suppressor, this will itself move in relation to the pipework branch concerned and be inserted into a gap in the said pipework, complex valve circuitry can be dispensed with. An ion-exchange chromatography device suitable for carrying out the method possesses, in addition to an analysis branch, a plurality of treatment branches that are each connected with a treatment agent source, so that a treatment agent can be fed through a suppressor that is inserted into such a pipework branch. Each of the pipework branches possesses a gap, and each of the suppressors is mounted to move in such a way that, in relation to each pipework branch, it can be brought into a position in which it bridges the gap, as a section of pipe, in the pipework branch concerned. The suppressors normally used possess a first connection opening that is connected with a second connection opening by a pipe section serving as an ion-exchange reservoir. The pipework branch gaps are determined in each case by two pipe openings. With that, for insertion into a pipework branch, each suppressor can be brought into a position in which each of its connection openings is aligned to one of the pipe openings determining the gap of the pipework branch concerned.

Preferably, at least the same number of suppressors are used as pipework branches, said suppressors being inserted alternatingly into the pipework branches in a fixed sequence wherein each suppressor has a predecessor and a successor. With that, during each analysis period, a suppressor is inserted into each pipework branch, and after in each case one analysis period, each suppressor inserted into in a pipework branch will be substituted by a successor. With this procedure, the pipework branches have a certain sequence, in which each suppressor is inserted consecutively into the individual pipework branches. The sequence of pipework branches is here selected according to the desired sequence of the cycle through which the suppressors should cyclically pass. As a rule, a first treatment branch, through which an acid or an alkaline solution can be fed for regeneration of a suppressor, will follow the analysis branch, and will in turn be followed by a second treatment branch, through which a neutral liquid such as water can be fed for rinsing of the suppressor. With this procedure, the treatment branches will be optimally exploited since, during each analysis period, a suppressor is inserted into each treatment branch. The suppressors can thus be regenerated particulary quickly so that, after a short analysis period, a regenerated suppressor will be ready and available for substitution of the suppressor inserted in the analysis branch.

Preferably, the suppressors are mounted in such a way that they can be moved on an endless track. The gaps in the pipework branches are here arranged in relation to this track in such a way that each suppressor can be inserted in any desired pipework branch by means of a movement along its track. The endless track can, for example, be a circular track, but can also be another type of endless track. Characteristic of the endless track is that a suppressor, if moved in one direction along its movement track, will eventually return to its starting point. The endless track is thus particularly suitable for sequential, cyclically repetitive insertion of a suppressor into a plurality of pipework branches. If there is a requirement for a movement along an endless track, this will basically concern the connection area of the suppressors, the said connection area requiring alignment to the gaps in the pipework branches. If, for example, a suppressor with two connection openings is concerned, in the sense of the definition used here, this shall count as being mounted on one endless track if, through movement of the suppressor, each of its connection openings are able to be moved along one endless track.

Basically, the individual suppressors can be mounted to be able to move on different tracks. To this end, it is of course necessary that the pipe openings of the gap of at least one pipework branch are larger than the connection openings of the suppressors, so that the connection openings of different suppressors can be aligned to different points on this pipe opening. This will be more closely explained in the following. A more simple construction of the entire arrangement is of course possible if all suppressors are mounted to be able to move on a common, endless track.

With the suppressors mounted to be able to move on an endless track, the effort required to substitute the suppressors inserted in the different pipework branches can be considerably reduced. To this end, the suppressors are coupled by an active connection in such a way that they can only be moved together, so that the position of one suppresor will depend on the position of the other suppressors. With that, the mutually connected suppressors are all able to be brought into a number of working positions corresponding to the number of suppressors, in which positions in each case another suppressor is inserted in the analysis branch. In the most simple case, here, too, an arrangement is concerned wherein all suppressors are mounted to move on a common, endless track. Adjacent suppressors can then be maintained at a definite distance, for example by means of a distance distance element serving as an active connection. For example, an endless link-chain running around over a plurality of chain wheels can be used, the individual suppressors being attached to the said link-chain. An alternative possibility comprises arranging the suppressors on the common movement track so closely that they make mutual contact. In this case, too, the suppressors can only be moved together, and in this sense an active connection will likewise arise between the suppressors. But also when all the suppressors do not lie on a common movement track, these can nevertheless be coupled to an active connection in order to facilitate alignment of the suppressors to the gaps in the pipework branches.

Due to the active connection existing between the suppressors, through insertion of a suppressor into the analysis branch, a supressor will likewise be simultaneously inserted into each further pipework branch. If the suppressors are mounted on a common, emdless track, they are preferably arranged to be distributed equidistantly along the length of the said track. The distances of the pipework branches, respectively their gaps, are with that adapted to the distance of the suppressors, so that one of the suppressors can be simultaneously inserted in each pipework branch.

A preferred way of creating an active link between the individual suppressors comprises fitting all suppressors to a common connecting body that is mounted to be able to move. At the same time, additional advantages will arise if the connection openings of the suppressors are located in an outer surface of the connecting body, and if the connecting body is mounted to move in such a way that the pipe openings of the pipework branches always lie within the area of this outer surface. With that, the pipe openings are closed by the outer surface of the connecting body, insofar that the connection opening of a suppressor is not located in their vicinity. During insertion of a suppressor, no liquid can thus escape from the pipe opening concerned.

Closing of the pipe openings by the outer surface of the connecting body as just described can also be exploited in order, with the suppressor inserted, to connect the areas of the pipe opening lying beyond the connection opening of the suppressor and aligned with said outer surface. With that, pipe openings that are larger than the connection openings of the suppressor can be used without problems. This advantage can be exploited in that a pipe opening is designed to be intentionally larger than the connection opening of the suppressors, so that the connection opening of different suppressors at differing positions can be aligned with this pipe opening. In place of a separate pipe opening, a plurality of partial openings can be used that are directly connected together by pipes. The connection openings of different suppressors can then be aligned to different partial openings of this pipe opening. According to the sense of the definition used here, the interconnected partial openings shall count as one pipe opening. Through the use of at least one larger pipe opening onto which the different connection openings of different suppressors at different points can be aligned, different advantageous possibilities will arise for alternating insertion of the suppressors, said suppressors being fitted to a common connecting body, into the different pipework branches, wherein mounting of the suppressors to be able to move on a common, endless track is unnecessary.

The cyclical substitution of the suppressors can be designed in a particularly simple way if the connecting body is mounted to rotate about a rotational axis so that each connection opening is able to be moved along a circular path. A cylindrical connecting body, for example, can be concerned, wherein the connection openings of the suppressors can either be provided in the wall surface or the facing surface of the cylinder.

In order to automate the cyclic regeneration of the supressors, each suppressor can be coupled to a movement drive, a control device being in turn connected with said movement drive. With that, through activation of the movement drive, each suppressor can be inserted into the different pipework branches.

Since, with the device described, frequent regeneration of the suppressors is also possible without problems and without obstructing the analysis procedure, suppressors are used that, in comparison to state of the art suppressor columns, have a relatively small volume, preferably between 50 and 500 mm$^3$. With that, the suppressor inserted in the analysis branch is preferably substituted after analysis of in each case one sample.

BRIEF DESCRIPTION OF THE DRAWINGS

The invention is more closely described in the following, with the aid of the embodiments: namely, FIG. 1 A schematic representation of a device for ion-exchange chromatography with one analysis branch and two treatment branches and with three suppressors that are inserted alternatingly into these pipework branches, FIG. 2 the device shown in FIG. 1 at another stage of the method, FIG. 3 a schematic representation of a device for ion-exchange chromatography, with three pipework branches and three suppressors, of which in each case one suppressor is inserted into each pipework branch, FIG. 4 a schematic representation of a device for ion-exchange chromatography with one analysis branch and one treatment branch, said treatment branch being able to be connected via a valve element selectively with one of two treatment agent sources, FIG. 5 a sectional drawing of the suppressor portion of a device for ion-exchange chromatography along the plane A—A in FIG. 6, FIG. 6 a sectional drawing along the line B—B in FIG. 5, FIG. 7 a sectional drawing of an alternative suppressor portion of a device for ion-exchange chromatography, along the plane C—C in FIG. 8, FIG. 8 a plan view of the suppressor portion shown in FIG. 7, and FIG. 9 a sectional drawing of a further suppressor portion in which the suppressors are fixed to a common connecting portion that is mounted to be linearly moveable.

DESCRIPTION OF THE PREFERRED EMBODIMENTS

Figure 1:
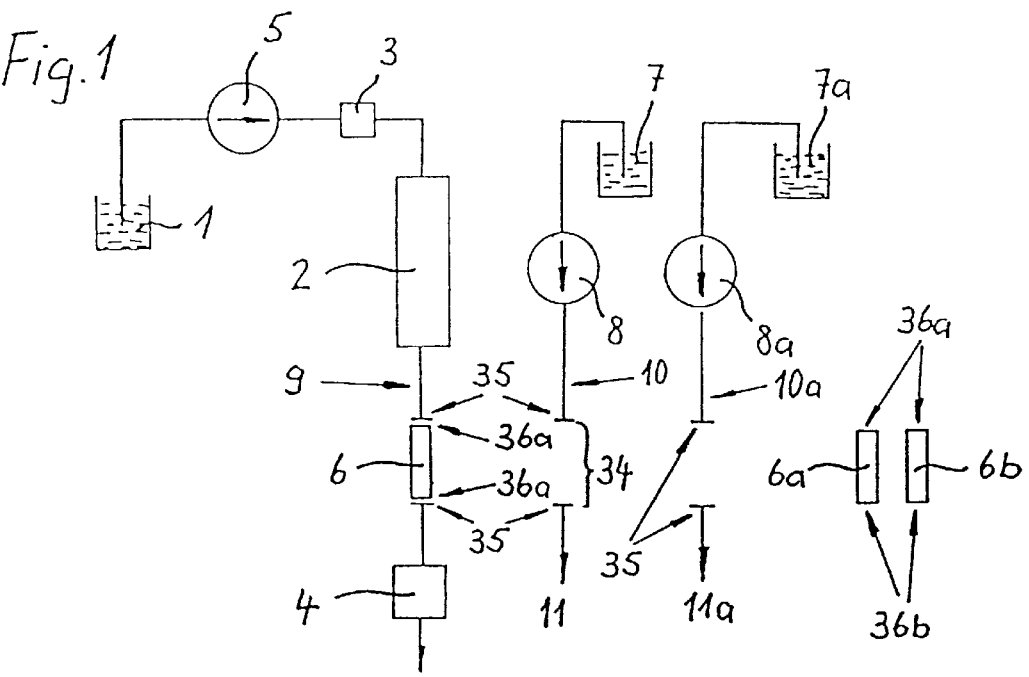

In FIG. 1, the device for ion-exchange chromatography shown in schematic form-possesses an analysis branch 9 and two treatment beanches 10, 10a. The analysis branch 9 connects the outlet of a separation column 2 to a detector 4. Detection of the separated ions as a rule ensues through measurement of conductivity. On the inlet side, an elution agent is fed to the separation column-via a pump 5. Equipment 3 for delivery of an analysis sample is located between the pump 5 and the separation column 2. A first suppressor 6 is inserted into the analysis branch 9. During analysis, the eluate running from the separation column 2 is fed through the first suppressor 6 and then to the detector 4. The suppressor 6 has the function of reducing the conductivity of the elution agent 1 so that the ions contained in the eluate running from the separation column 2 can be detected more precisely. With that, ion exchange will take place within the suppressor 6, and with time the capacity of the suppressor will be exhausted.

The suppressor 6 inserted into the analysis branch 9 must for this reason be regenerated from time to time. In order to be able to carry out further analyses during regeneration of the suppressor, after in each case one analysis period, the suppressor 6 inserted into the analysis branch 9 will be substituted by a regenerated suppressor. Two treatment branches 10, 10a are provided for regeneration of the substituted suppressor, each treatment branch being connected via a pump 8, 8a in each case to a treatment agent source 7, 7a. On the other side, the treatment branches 10, 10a are connected to drain pipes 11, 11a. In order to be able to insert the suppressors into the different pipework branches 9, 10, 10a, each of these pipework branches possesses a gap 34 that is defined by two pipe openings 35. The suppressors 6, 6a, 6b each have a first connection opening 36a that is connected by a pipework section serving as an ion-exchange reservoir, said pipework section possessing a second connection opening 36b. The individual suppressors are now mounted to be able to move in such a way that they can be inserted into the different pipework branches. If a suppressor 6 is inserted into pipework branch 9, then the connection openings 36a, 36b will be aligned with the pipe openings 35 of the gap of this pipework branch 9. The suppressor 6, as a pipe section, thus bridges the gap in the pipework branch 9.

Figure 2:
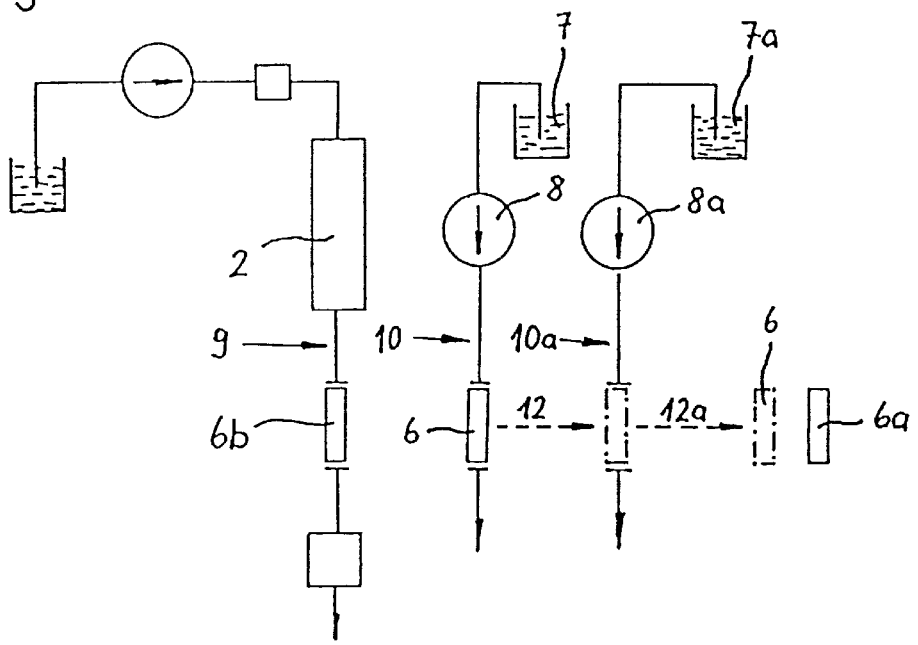

In FIG. 2, the same device is represented at a somewhat later point in time, after the suppressor 6 has been substituted with a regenerated suppressor 6b. The substituted suppressor 6 has been inserted into the first treatment branch 10 and, for regeneration, an acid is pumped through the substituted suppressor 6 via the pump 8. After a specific time, the suppressor 6 is removed from the first treatment branch 10 and moved in the direction of the arrow 12 to the gap of the second treatment branch 10a, and inserted there. Subsequently, water is pumped through the suppressor 6 via the pump 8a. Finally, the then once again completely regenerated suppressor 6 is removed from the second treatment branch 10a and brought to a standby position in the direction of the arrow 12a, in which it assumes the original position (see FIG. 1) of the suppressor 6a. In a next step, the suppressor 6b by this time inserted in the analysis branch 9 would be substituted by the regenerated suppressor 6a, and the suppressor 6b would be inserted consecutively into the treatment branches 10, 10a, in the same way as for the case just described for the suppressor 6. The suppressors 6, 6a, 6b are cyclically inserted into the pipework branches 9, 10, 10a, one of the suppressors being inserted into the analysis branch 9 during in each case one analysis period.

With the example just described, two completely regenerated suppressors are always available before the third suppressor, inserted in the analysis branch, requires substitution. Evidently, with an otherwise similar sequence for the method, one of the suppressors could be dispensed with.

Figure 3:
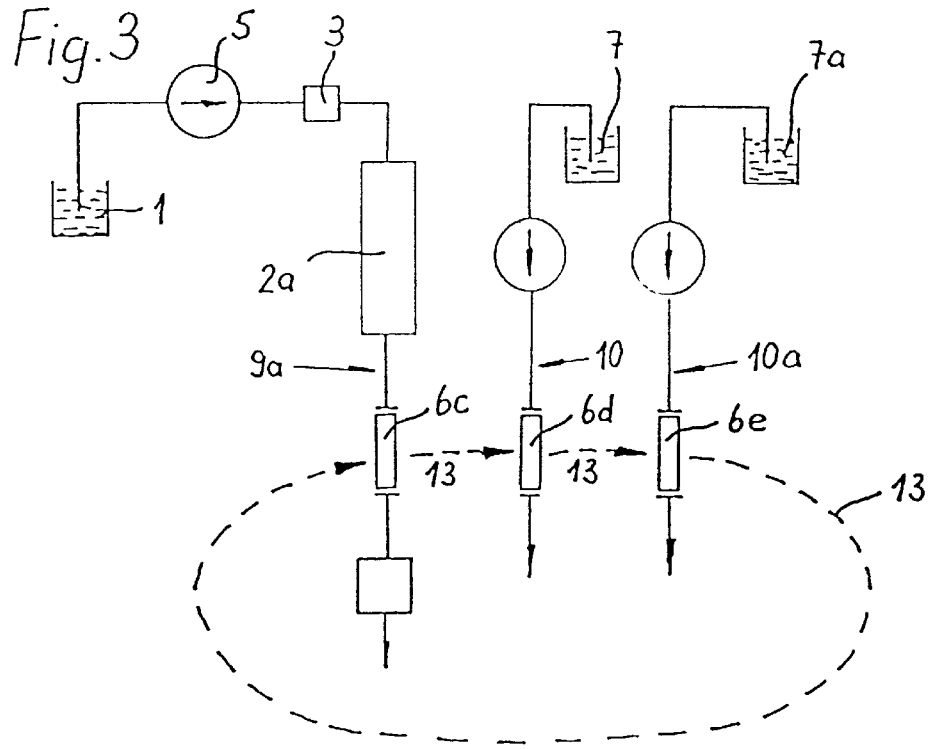

In the examples shown in FIGS. 1 and 2, the basic principle of the device has been shown. For practical reasons, however, a slightly modified sequence is preferred for the method. Such a preferred modified..sequence is shown in FIG. 3. The device according to FIG. 3 corresponds in principle to all the points of that shown in FIGS. 1 and 2. It differs solely in the position of the suppressors. During an analysis period, a suppressor 6c, 6d, 6e is located in each pipework branch 9a, 10, 10a. This has numerous advantages: for most of the time, a suppressor is inserted into each pipework branch so that escape of treatment liquid from temporarily unoccupied gaps can be prevented. Apart from that, the time of an analysis period can be fully used for the regeneration of the suppressors 6d, 6e inserted into the treatment branches 10, 10a. The standby positions of the suppressors 6a and 6b shown in FIG. 1 are dispensed with since, in the arrangement according to FIG. 3, the suppressor 6e inserted into the second treatment branch 10a is, at the next change-over, inserted directly into the analysis branch, 9a as the regenerated suppressor. Further advantages will result in relation to the construction of the required device, as is apparent in FIGS. 5 to 8.

Figure 4:
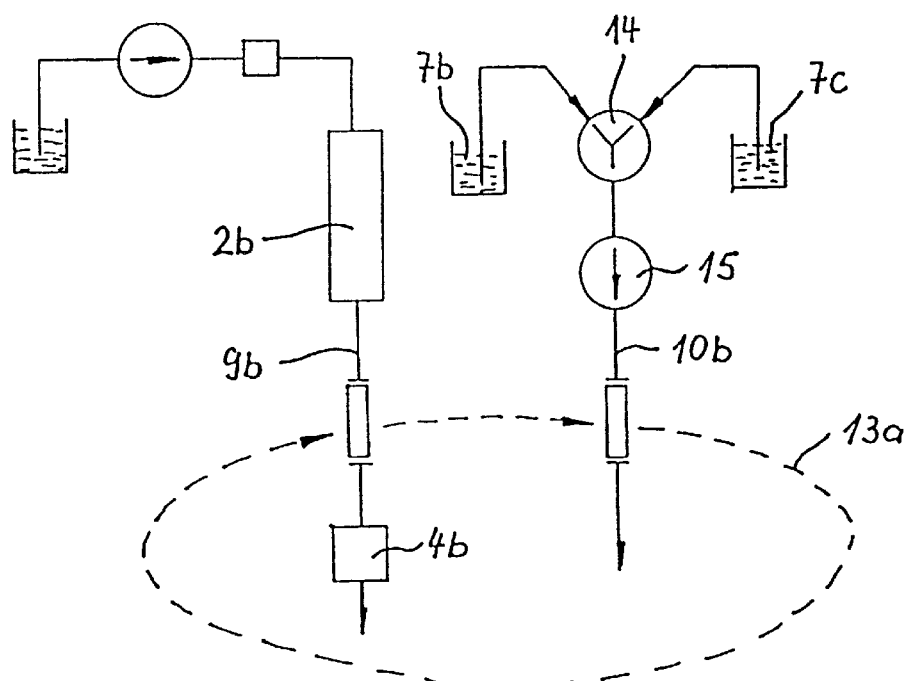

In schematic form, FIG. 4 shows a device for ion-exchange chromatography with only two pipework branches 9b and 10b. The procedure during cyclical substitution of the suppressors corresponds to that described in relation to FIG. 3. However, the single treatment branch 10b can be selectively connected via a switching valve 14 with one of a plurality of treatment agent sources 7b, 7c.

Figure 5:
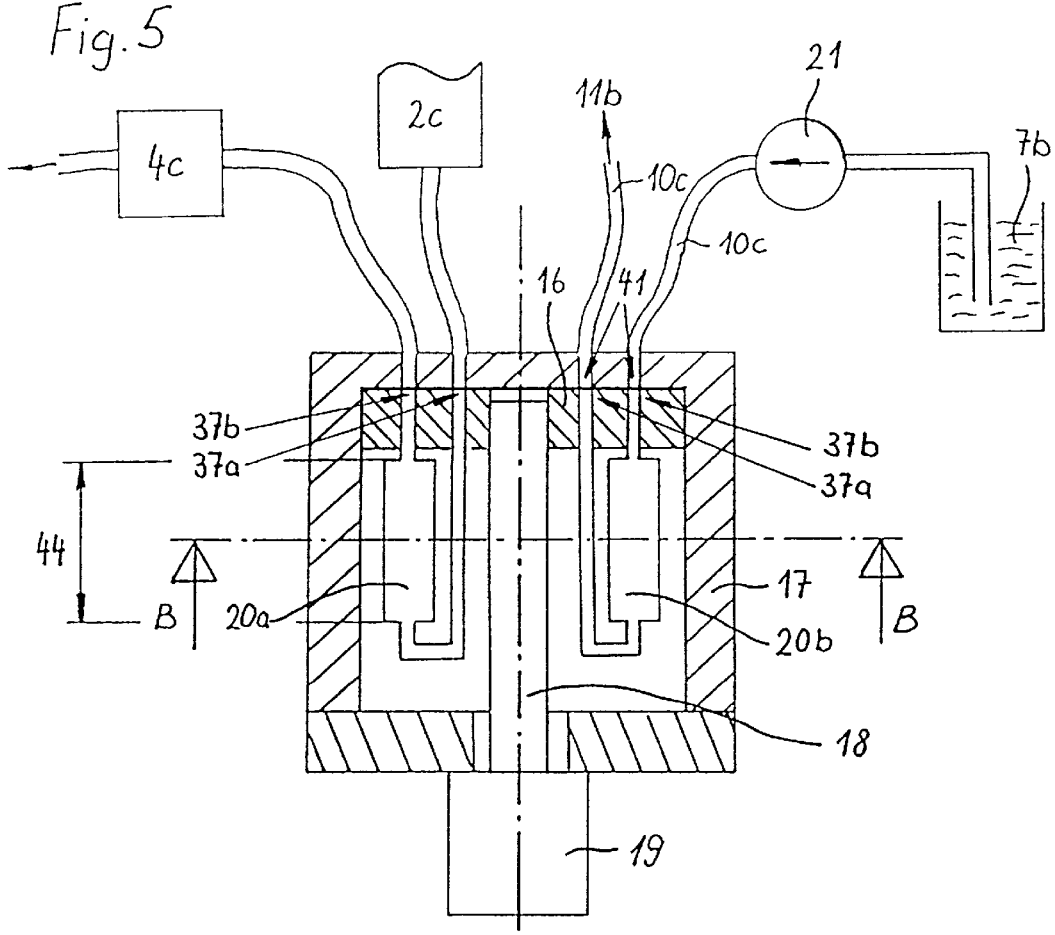
Figure 6:
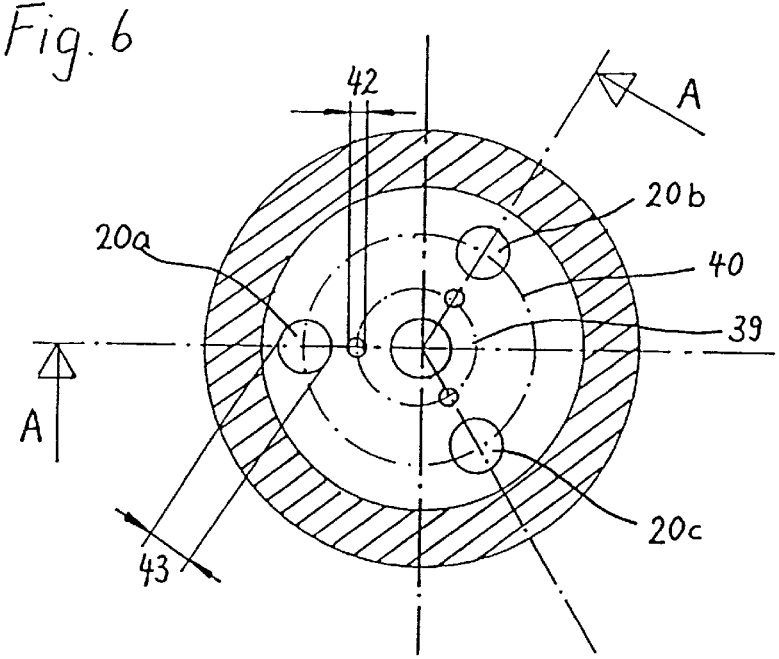

FIG. 5 shows a sectional representation of a suppressor arrangement for a device for ion-exchange chromatography as schematically shown in FIG. 3. In FIG. 6, a sectional drawing along the line B—B in FIG. 5 is shown. The arrangement contains 3 suppressors 20a, 20b and 20c, that are attached to a common connecting body 16. The connecting body 16 is mounted to rotate in a housing 17, and is connected by a rotary shaft 18 with a motor 19 serving as a movement drive. All first connection openings 37a lie on a first circular line 39, and all second connection openings 37b lie on a second circular line 40, the centres of the two circles coinciding with the rotational axis of the connecting body 16. Through rotation of the connection body 16, all the first connection openings are able to be moved along a first circular path 39, and all the second connection openings are able to be moved along a second circular path 40. With these circular paths, a special form of endless track is concerned, along which the suppressors, respectively the connection openings are able to be moved. The suppressors are, apart from that, arranged to be distributed equidistantly along the length of these circular paths.

The pipe openings 41 of the gaps of three pipework branches are arranged equidistantly along these circular paths, of which, however, only two 9c, 10c, are shown in FIG. 5. The pipework 9c is an analysis branch that connects the outlet of separation column 2c with a detector 4c. The pipework branch 10c is a treatment branch that on one side is connected with the treatment agent source 7b and on the other side leads to a drain 11b. By rotating the common connecting body 16, the said connecting body for this purpose being coupled to a rotational drive 19, the individual suppressors 20a to 20c can be inserted alternatingly into the individual pipework branches according to the method described in relation to FIG. 3.

In this example, the connection openings 37a and 37b are located in an outer surface of the connecting body 16. By means of the aforementioned mounting of this connecting body, it is ensured that the pipe openings 41 of the gaps of the different pipework branches are always located in the area of this outer surface, which in this case is the facing surface of the connecting body. Hence, on rotation of said connecting body, the pipe openings 41 will be closed by the outer surface of the connecting body, insofar as the connection opening 37a, 37b of a suppressor is not located in the vicinity of a pipe opening. It is thus ensured that the liquids transported in the pipework branches can at no time escape in the vicinity of the pipe openings.

It must be pointed out that in FIGS. 5 to 9, actual relative sizes are not reproduced true to scale. As a rule, capillary tubes with an inside diameter of approx. 0.2 to 0.5 mm are used as connecting pipes in liquid ion-exchange chromatography. The slightly thicker bodies 20a to 20c of the suppressors, filled with ion-exchange resin, preferably have an inside diameter 43 of 2 to 5 mm, and a length 44 of approx. 20 to 50 mm.

It should also be-pointed out that the number of suppressors and pipework branches used in an arrangement according to FIG. 5 can be changed without problems. In particular, only two suppressors and two pipework branches can be used, so that an arrangement according to the principle represented in FIG. 4 can be realised. Apart from that, more suppressors than pipework branches can be used without problems. There will be no resultant change to the structure of the device.

Figure 7:
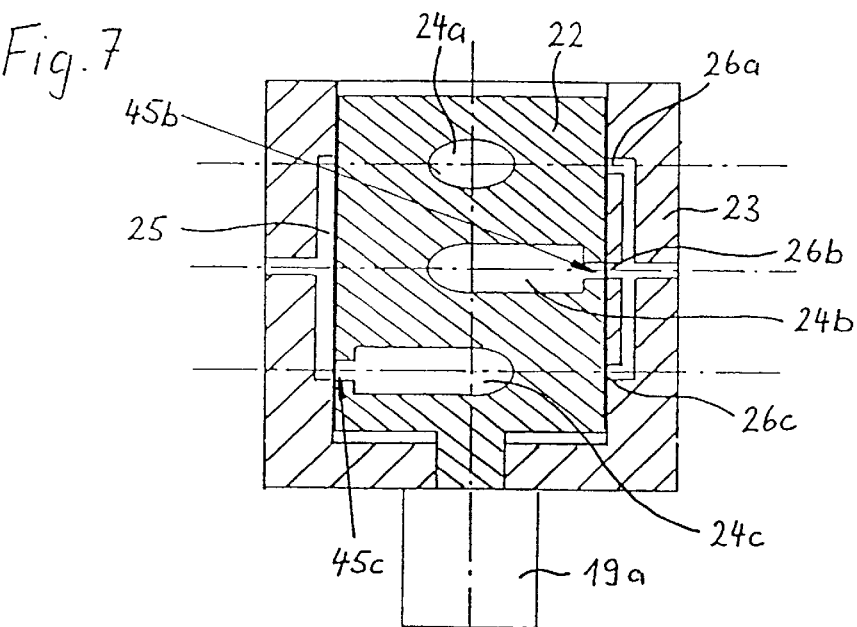
Figure 8:
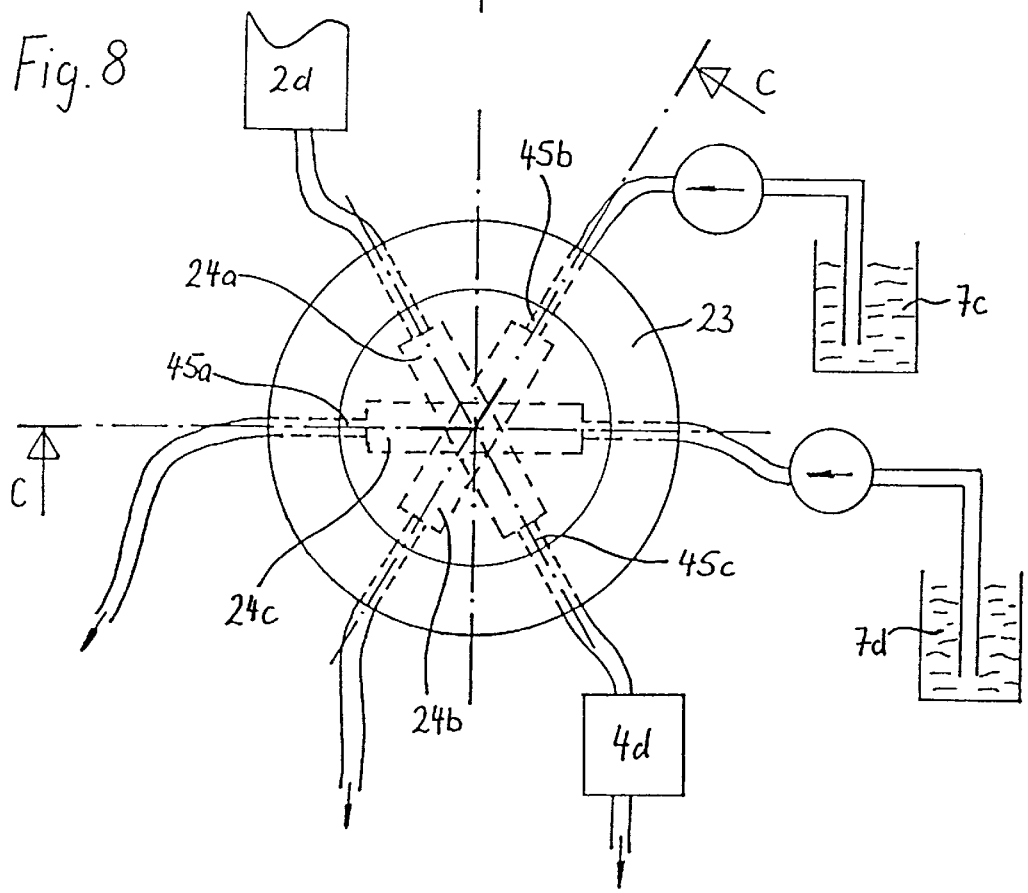

FIGS. 7 and 8 show an alternative embodiment of an arrangement of suppressors, FIG. 7 showing a sectional representation along the plane C—C in FIG. 8. Here, too, three suppressors 24a to 24c are used, attached to a common connecting body 22. The connecting body is a cylindrical connecting body that is mounted to rotate around its body axis. Here, too, each suppressor 24a to 24c has two connection openings 45a to 45c arranged on opposite sides in the wall surface of the cylindrical connecting body 22. The suppressors in this example are arranged to be distributed along the length of the cylindrical connecting body and, as opposed to the example shown in FIG. 5, it is here not possible to bring the connection openings of the individual suppressors alternatingly into the same position. In order to nevertheless insert the suppressors alternatingly into the three pipework branches shown in FIG. 8, larger pipe openings are used for determination of the gaps of the pipework branches, so that it is nevertheless possible to insert each suppressor into each of the pipework branches. With that, the connection openings of the different suppressors are aligned at different points with the specially enlarged pipe openings. In FIG. 7, two different possibilities for enlargement of the pipe openings are shown. The pipe opening 25 shown in the left half of FIG. 7 is a longitudinal slit that extends over a considerable portion of the length of the tubular housing 23 in which the connecting body 22 is mounted to be able to rotate. Evidently, the portion of the pipe opening 25 not aligned with the connection opening 45c will be closed by the outer surface of the cylindrical connecting body. On the right-hand side of FIG. 7, an alternative embodiment is shown with which a plurality of partial openings 26a to 26c are provided in place of a longitudinal slit 25, and are interconnected by pipes.

The connecting body 22 is coupled to a rotational drive 19a for automatic exchange and regeneration of the suppressors.

Figure 9:
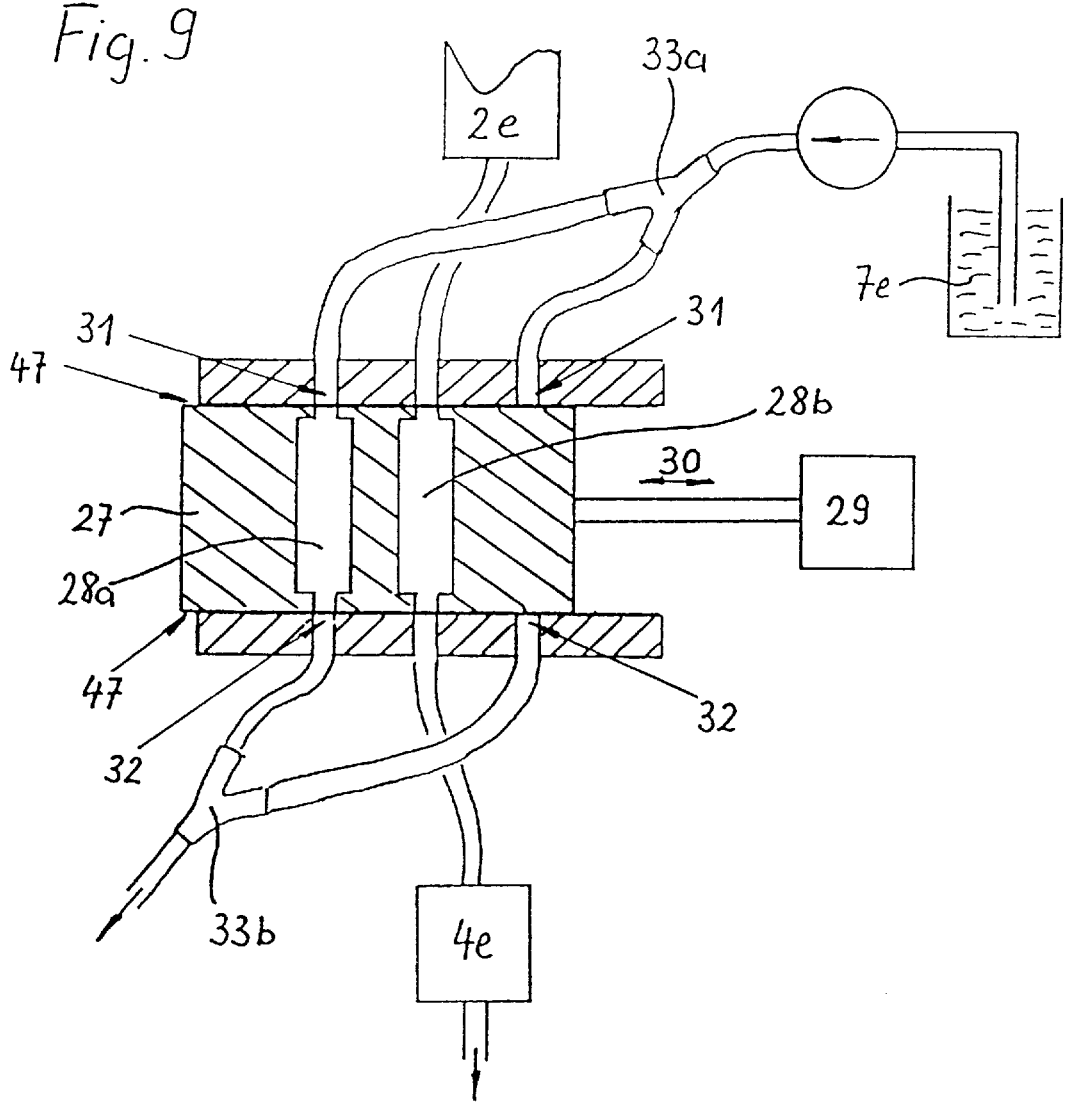

Finally, FIG. 9 shows a sectional drawing of a further embodiment of an arrangement of suppressors, wherein the suppressors 28a, 28b are likewise fixed to a common connecting body 27. Here, exceptionally, this is not a connecting body mounted to rotate, but a body mounted to be able to slide linearly, and possessing two parallel limiting surfaces 47. To a large degree, the functional principle nevertheless corresponds with the example shown in FIG. 7. In this case, there is only one pipework branch, the pipe openings of which comprise a plurality of interconnected partial openings 31, 32. Here, too, the partial openings that are "not required" are closed by the outer surface 47 of the common connecting body 47. The connecting body 27 is mounted to be able to move in the direction of the arrow 30, and coupled to a linear drive 29. Such an arrangement could, for example, be used in a device according to FIG. 4. With only inconsequential extra effort, this arrangement can also be extended by one treatment branch and an additional suppressor, so that operation according to the method described in FIG. 3 is possible. With that, the connecting body would preferably be moved in an additional direction, so that it would be able to be brought cyclically and alternatingly into three different positions.

Inasmuch as the invention is subject to modifications and variations, the foregoing description and accompanying drawings should not be regarded as limiting the invention, which is defined by the following claims and various combinations thereof:

We claim:

1. A method for cyclically regenerating a suppressor in an ion chromatography process, said method comprising steps of
    a) suppressing an eluate exiting from a separator column in a first suppressor inserted into an analysis flow line branch connecting the outlet of said separator column with a detector,
    b) during step (a), treating a second suppressor inserted in a treatment flow line branch carrying a treatment fluid,
    c) after steps (a) and (b), removing said second suppressor from said treatment flow line branch, removing said first suppressor from said analysis flow line branch, moving said first suppressor relative to said analysis flow line branch and inserting said first suppressor into said treatment flow line branch, and
    d) repeating step (b) with said first suppressor and repeating step (a) for said second suppressor.

2. A method according to claim 1 wherein during steps (a) and (b), a third suppressor is inserted in a second treatment flow line branch carrying rinsing water and wherein after step (c), said second suppressor is inserted into said second treatment flow line branch and said third suppressor is inserted into said analysis flow line branch.

* * * * *